(12) United States Patent
Polegato Moretti

(10) Patent No.: US 7,458,288 B2
(45) Date of Patent: Dec. 2, 2008

(54) APPARATUS FOR SIMULATING THE PERSPIRATION OF THE HUMAN BODY AND FOR ASSESSING THE VAPOR PERMEABILITY AND COMFORT OF AN ITEM OF CLOTHING

(75) Inventor: Mario Polegato Moretti, Crocetta del Montello (IT)

(73) Assignee: Geox S.p.A., Montebelluna (IT)

( * ) Notice: Subject to any disclaimer, the term of this patent is extended or adjusted under 35 U.S.C. 154(b) by 0 days.

(21) Appl. No.: 11/562,653

(22) Filed: Nov. 22, 2006

(65) Prior Publication Data
US 2007/0151374 A1    Jul. 5, 2007

(30) Foreign Application Priority Data
Dec. 13, 2005    (IT) .......................... PD2005A0363

(51) Int. Cl.
*G01N 17/00*    (2006.01)
(52) U.S. Cl. .................................... 73/865.6
(58) Field of Classification Search ........................ None
See application file for complete search history.

(56) References Cited

U.S. PATENT DOCUMENTS 5,749,259 A * 5/1998 Hamouda et al. ............. 73/159

2002/0191669 A1 * 12/2002 Fan et al. ...................... 374/45
2004/0008751 A1 * 1/2004 Polegato Moretti et al. ... 374/45
2004/0118228 A1 * 6/2004 Puckett et al. .............. 73/866.4

FOREIGN PATENT DOCUMENTS

| EP | 0 837 329 A1 |   | 4/1998 |
|----|----|----|----|
| JP | 401138440 | * | 5/1989 |
| JP | 5-18591 |   | 1/1993 |
| JP | 10-332683 |   | 12/1998 |
| JP | 410332683 | * | 12/1998 |

* cited by examiner

*Primary Examiner*—Robert R Raevis
(74) *Attorney, Agent, or Firm*—Oblon, Spivak, McClelland, Maier & Neustadt, P.C.

(57) ABSTRACT

An apparatus for simulating perspiration of human body and for assessing the vapor permeability and comfort of an item of clothing, comprising:
- a manequin body, provided internally with a cavity, which is contoured so as to wear the item of clothing to be tested and has on its surface a plurality of through holes which open onto the cavity;
- an external surface covering for the body, which is vapor-permeable and has water vapor absorption and release properties:
- elements for generating water vapor which are adapted to supply the cavity directly with vapor.

18 Claims, 2 Drawing Sheets

APPARATUS FOR SIMULATING THE PERSPIRATION OF THE HUMAN BODY AND FOR ASSESSING THE VAPOR PERMEABILITY AND COMFORT OF AN ITEM OF CLOTHING

The present invention relates to an apparatus for simulating the perspiration of the human body and for assessing the vapor permeability and comfort of an item of clothing, particularly but not exclusively for jackets and trousers.

BACKGROUND OF THE INVENTION

As is known, human perspiration occurs by expelling sweat through the pores of the skin, each pore being connected to sweat glands.

The generated sweat is liquid, and once it has come into contact with the warm skin it evaporates, removing its own latent heat of evaporation (approximately 580 calories/g at 30° C.).

This cools the skin and activates the phenomenon of body thermoregulation.

It is rather simple to deduce, therefore, that ventilation and vapor permeability of items of clothing are key factors in the dissipation of the metabolic heat of the body.

Currently there are no methods and devices for measuring the vapor permeability of items of clothing such as jackets or trousers which take into consideration the entire item.

Currently known methods are in fact limited exclusively to the component materials, allowing to obtain data related to vapor permeability defined in milligrams per square centimeter per hour or in grams per square centimeter per day, but do not take into consideration the actual structure of the item.

Therefore, in practice there are no methods for determining simply the amount of water vapor or more generally the amount of humidity that is present within a complete item of clothing.

SUMMARY OF THE INVENTION

The aim of the present invention is therefore to provide an apparatus which is capable of simulating the mass and energy exchange phenomena that occur between the human body and the outside environment and can therefore assess the vapor permeability performance of entire items of clothing.

Within this aim, an object of the present invention is to provide an apparatus adapted to simulate the perspiration of the human body which allows to assess the vapor permeation and objective comfort provided by an item of clothing.

Another object of the present invention is to provide an apparatus adapted to simulate the perspiration of the human body which allows to assess the vapor permeation and objective comfort provided by an item of clothing end which provides accurate and reproducible results which can be influenced only to a limited extent by operator errors.

Another object of the present invention is to provide an apparatus which is capable of determining the vapor permeability value of an item of clothing, avoiding subjective thermal-physiological tests.

Still another object of the present invention is to provide an apparatus for simulating the perspiration of the human body and for assessing the vapor permeability and comfort provided by an item of clothing which is structurally simple and easy to use.

This aim and these and other objects, which will become better apparent hereinafter, are achieved by an apparatus for simulating the perspiration of the human body and for assessing the vapor permeability and comfort of an item of clothing, characterized in that it comprises:

a mannequin-like body, provided internally with a cavity and contoured so as to wear the item of clothing to be tested, said mannequin-like body having on its surface a plurality of through holes which open onto said cavity, an external surface covering for said mannequin-like body, which is vapor-permeable and has water vapor absorption and release properties, means for generating water vapor which are adapted to supply said cavity directly with vapor.

BRIEF DESCRIPTION OF THE DRAWINGS

Further characteristics and advantages of the invention will become better apparent from the description of a preferred but not exclusive embodiment thereof, illustrated by way of non-limiting example in the accompanying drawings, wherein.

Figure 1:
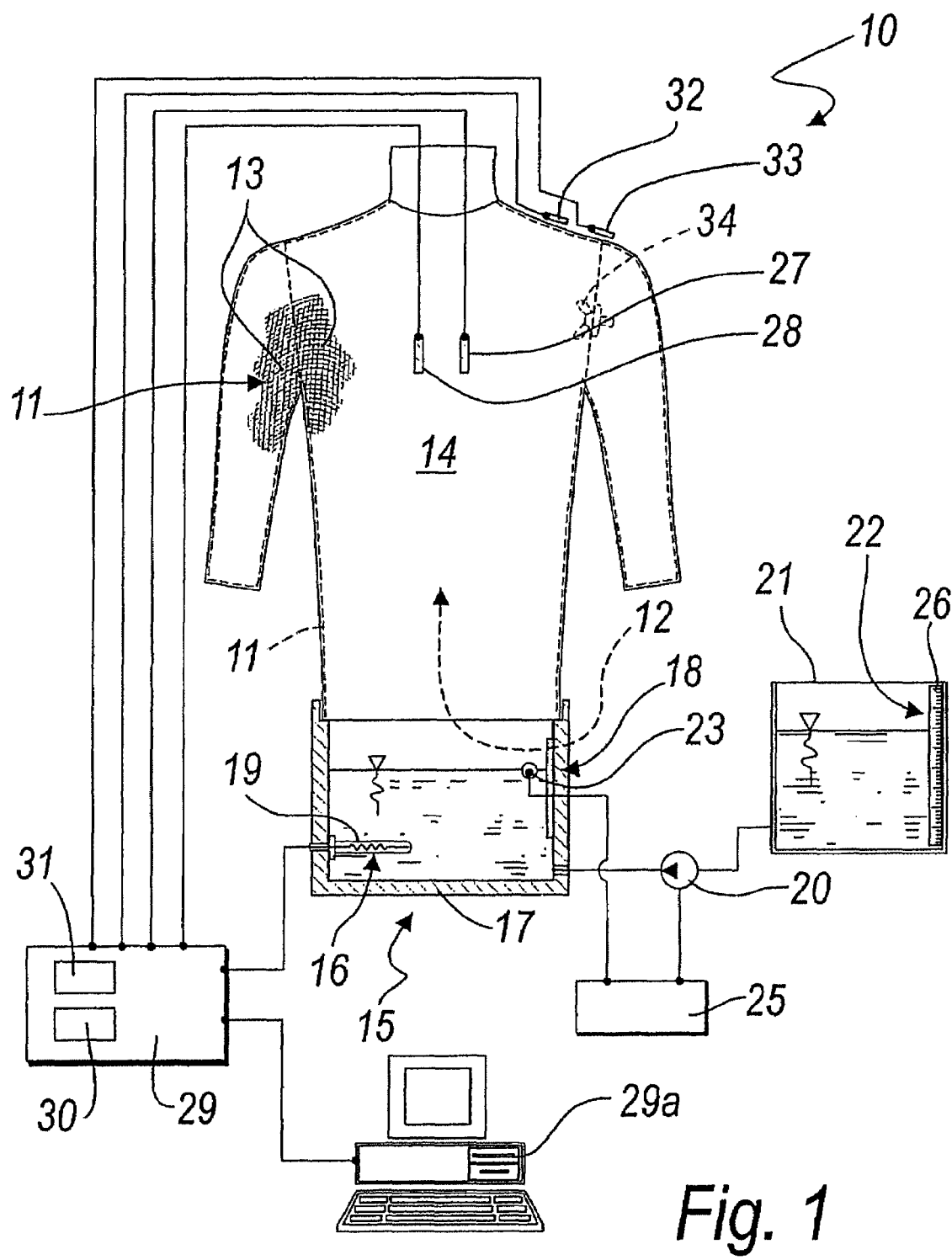
FIG. 1 is a schematic view of an apparatus according to the invention.

It is noted that anything found to be already known during the patenting process is understood not to be claimed and to be the subject of a disclaimer.

DESCRIPTION OF THE PREFERRED EMBODIMENTS

With reference to the figures, an apparatus for simulating the perspiration of the human body and for assessing the vapor permeability and comfort of an item of clothing, according to the invention, is generally designated by the reference numeral 10.

The apparatus 10 for measuring the vapor permeability and comfort of an item of clothing comprises a mannequin-like body 11, provided internally with a cavity 12 and contoured so as to wear the item of clothing to be tested; in this embodiment, the mannequin-like body 11 is contoured like a human trunk.

As clearly shown in the figures, the mannequin-like body 11 is provided on its surface with a plurality of through holes 13 which open onto the cavity 12.

In particular, in this embodiment, the mannequin-like body 11 is formed by a net of self-supporting rigid material, the meshes of which define the through holes 13.

An external surface covering 14, in practice a vest, is associated with the mannequin-like body 11.

In FIG. 1, the mannequin-like body is predominantly covered by the vest and its outline is marked in broken lines; a cutout of the outer surface covering 14 is simulated in the armpit region in order to show the net that constitutes the mannequin-like body.

The part of the mannequin-like body 11 related to the neck is preferably not perforated.

The outer surface covering 14 is made of a vapor-permeable material which can absorb water vapor and release it.

In this embodiment, the outer surface covering 14 is made of textile material, such as for example a natural fiber (for example cotton) or a synthetic fiber.

In other embodiments, the outer surface covering 14 can be made of a non-woven material, such as for example a vapor-permeable membrane.

In the described embodiment, means for dressing and undressing the mannequin-like body 11 are associated with the outer surface covering 14 and are constituted for example by engagement and disengagement means 34 for the arms of the mannequin-like body 11, which facilitate dressing, and by the elasticity of the fabric of the covering.

In other variations, the means for dressing and undressing the mannequin-like body 11 can comprise zip fasteners, buttons or others.

The apparatus 10 further comprises water vapor generation means 15, which are adapted to supply the cavity 12 directly.

The water vapor generation means 15 comprise, in this embodiment, a first water tank 17, which is connected directly to the cavity 12 and in which there are first means 18 for measuring the level of the water and means 16 for heating the water that is present; the latter means are constituted by at least one resistive heating element 19, which is provided inside the first tank 17 and is connected electrically to an electrical power supply (not shown in the figures).

The resistive heating element 19 heats the water of the first tank 17, generating steam which rises within the cavity 12.

The first tank 17 is in fact arranged below the mannequin-like body 11, whose cavity 12 forms the top of said first tank 17; the first tank 17 constitutes the footing for the mannequin-like body 11.

The first tank 17 is supplied by a precision pump 20, which draws from a second top-up water tank 21.

In particular, said first means 18 for measuring the water level are constituted by a level sensor 23, which is functionally connected to the actuation of the pump 20; for example, the level sensor 23 is connected electrically to an electronic control unit 25, to which the electric motor drive of the pump 20 is connected electrically.

When the level of the water of the first tank varies by a minimum programmed threshold, the electronic control unit 25 drives the pump 20 so as to restore the correct level (as will become better apparent hereinafter, the level of the first tank 17 must remain constant).

Second means 26 for measuring the water level are associated with the second tank 21, such as, in this embodiment, a simple graduated water level indicator, which indicates the free surface of the water that is present (it is evident that in other embodiments such second water level measurement means can be of another type, even an electronic type).

The second means 26 for measuring the level of the water within the second tank 21 in practice define means 22 for measuring the amount of water used to generate steam, as will become better apparent hereinafter.

The apparatus 10 further comprises temperature sensing means 27 and humidity sensing means 28, which are arranged inside the cavity 12 and are interfaced with a central electronic management and control unit 29 (which in turn is, for example, associated with a personal computer 29a).

The temperature sensing means 27 are constituted for example by thermocouple sensors, while humidity sensor means 28 are constituted for example by capacitive sensors.

It is evident that in other embodiments the level sensor 23 and the electric motor drive of the pump 20 also can be interfaced with the central electronic management and control unit 29 (which in general may manage all the components associated with an electrical signal).

The resistive heating elements 19 also are interfaced with the central electronic management and control unit 29, and heat regulators 30 are also associated therewith in order to be able to set the correct temperature in the first tank 17.

Advantageously, means 31 for measuring the power used to operate the water vapor generation means 15 are provided, such as for example a wattmeter for measuring the power dissipated by the resistive heating elements 19 that constitute the means 16 for heating the water that is present in the first tank 17.

Depending on the requirements, the apparatus 10 further comprises additional temperature sensing means 32 and humidity sensing means 33, which are arranged in contact with, or at a certain distance from, the outer surface of the external surface covering 14, in practice within the interspace formed between the inside of the item of clothing (designated by the reference letter A in FIG. 2) and said external surface covering 14.

Operating principle of the apparatus is as follows.

The water, taken from the second graduated tank 21, is conveyed into the first tank 17 and kept at a constant temperature by the resistive heating elements 19.

The temperature sensing means 27 and the humidity sensing means 28, arranged inside the cavity 12 (in a central position thereof), provide information for setting the temperature of the water of the first tank 17 so as to generate an amount of water vapor at the selected temperature, preferably similar to the temperature of human skin, in particular approximately 36-37° C., and sufficient to fill uniformly the cavity 12 and moisten the external surface covering 14, simulating human perspiration.

The flow of water is adjusted for testing at a constant flow-rate.

Figure 2:
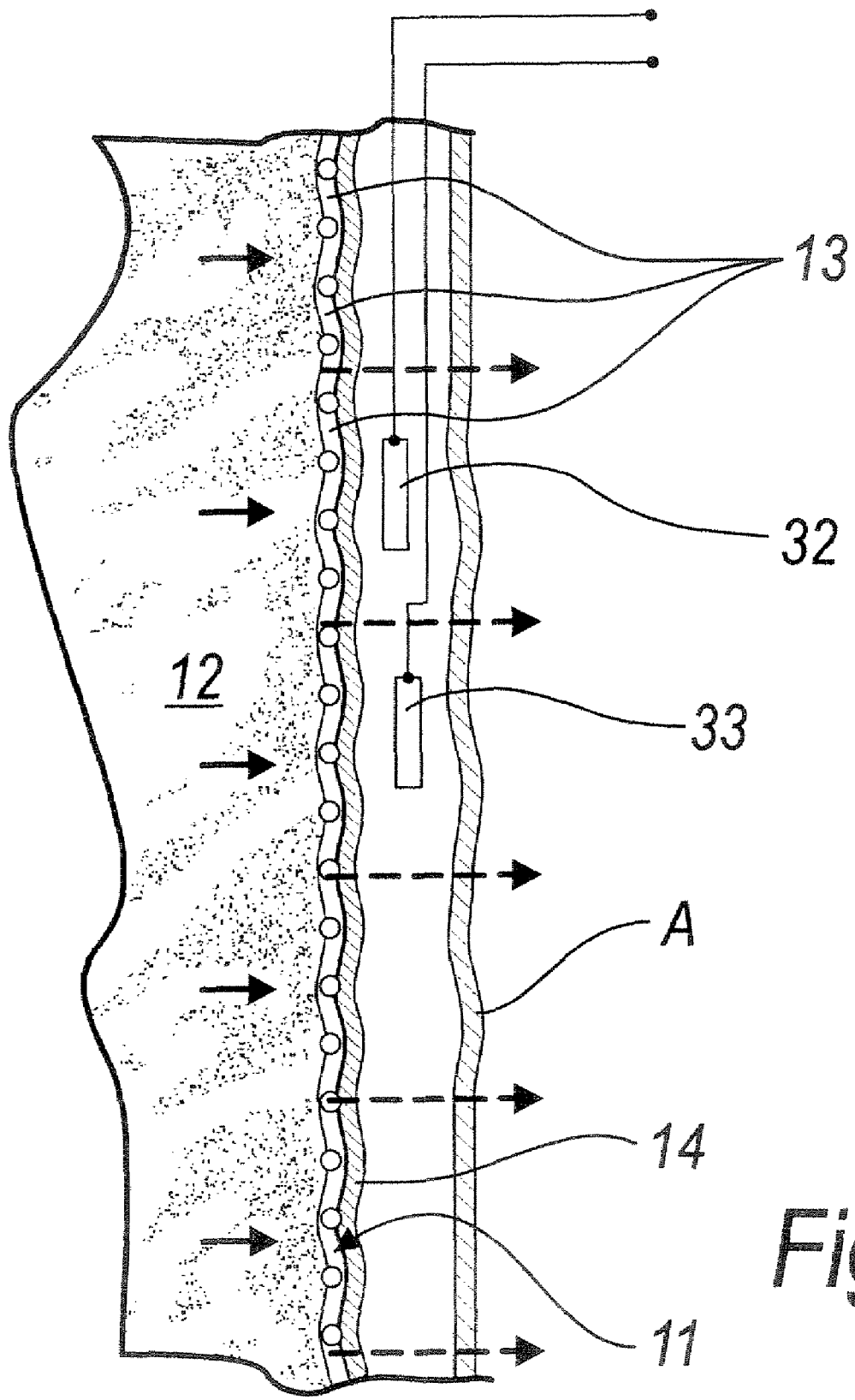
FIG. 2 is a schematic sectional view of a portion of the apparatus wearing an item of clothing.

The mannequin-like body 11 is dressed with the item of clothing A to be examined and it is possible to insert the additional temperature sensing means 32 and humidity sensing means 33 capable of characterizing the microclimate that is produced between the internal wall of the item of clothing A and the external surface covering 14 (vest); reference is made to FIG. 2.

A known amount of water is supplied to the first tank 17 and its weight distribution in the different layers is then checked at the end of the test (item of clothing, vest, tanks).

The wattmeter allows to measure dissipation of the energy used to provide the water vapor.

The amount of humidity and of heat that the mannequin-like body 11 releases are thus monitored and measured precisely by means of the dissipation of energy and water.

In order to obtain reproducible results and eliminate the variability due to environmental climate conditions, the tests must be carried out in a controlled environment at constant temperature and humidity and in particular at a temperature of 20° C. and at 65% relative humidity.

The testing method, related to the apparatus according to the invention, comprises the following sequence of operations.

First of all, an external surface covering, hereinafter referenced simply as "vest" 14, is conditioned, and so is an item of clothing A for each test, for at least 24 hours in a climate-controlled environment at a temperature of 20° C. and 65% relative humidity.

After the first test, it is possible to speed up the acclimatization time by means of a ventilated oven, making sure that the weights of the covering (vest) and of the item of clothing return to the same value obtained after the first 24 hours of conditioning.

The first tank 17 and the second tank 21 are then filled with a predefined amount of water.

The water of the first tank 17 is then heated to a predefined temperature, for example 60° C.

The mannequin-like body 11 is dressed with a vest for conditioning.

The system is then conditioned for a predefined time, in particular for at least 30 minutes, checking with the temperature sensing means 27 and humidity sensing means 28 that the internal temperature of the water vapor reaches 36-37° C. and relative humidity reaches 100% (saturation).

The test vest and the item of clothing are then weighed.

The conditioning vest is rapidly replaced with the test vest and the mannequin is dressed with the item of clothing.

After a preset time, in particular 60 minutes, the test vest and the item of clothing are weighed again.

In practice it has been found that the invention thus described achieves the intended aim and objects.

In particular, the present invention provides an apparatus which is capable of simulating realistically the perspiration of the human body and of assessing adequately the vapor permeability and comfort of an item of clothing.

The apparatus can be applied conveniently to any type of item of clothing: the mannequin-like body can in fact be provided in any shape: a trunk with or without arms, with or without legs, with or without a head, just the legs, et cetera, and thus can be used for vests, shirts, jackets, coats, trousers, shorts, underpants, et cetera.

The measurements of absorption and of release of humidity of the vest and of the item of clothing being tested characterize the comfort generated by the item of clothing, while the difference between the measurement of the consumption of water during the test and the measurements of water vapor absorption of the vest and of the item of clothing provide an indication of the vapor permeation of the item of clothing.

The invention thus conceived is susceptible of numerous modifications and variations, all of which are within the scope of the appended claims; all the details may further be replaced with other technically equivalent elements.

In practice, the materials used, so long as they are compatible with the specific use, as well as the dimensions, may be any according to requirements and to the state of the art.

The disclosures in Italian Patent Application No. PD2005A000363 from which this application claims priority are incorporated herein by reference.

What is claimed is:

1. An apparatus for simulating perspiration of human body and for assessing vapor permeability and comfort of an item of clothing, comprising:
   a mannequin body, provided internally with a cavity and contoured so as to wear an item of clothing to be tested, said mannequin body having on a surface thereof a plurality of through holes which open onto said cavity,
   an external surface covering for said mannequin body, which is vapor-permeable and has water vapor absorption and release properties,
   means for generating water vapor which are adapted to supply said cavity directly with vapor at a temperature proximate to the temperature of human skin.

2. The apparatus according to claim 1, wherein said water vapor generation means includes means for measuring an amount of water used to generate the vapor.

3. The apparatus according to claim 2, wherein said water vapor generation means further comprises
   a first water tank, which is connected directly to said cavity and in which there are first means for measuring a level of water and means for heating the water that is present,
   a second top-up water tank, with which second water level measurement means are associated, said second tank being functionally connected to said first tank by means of a pump, said second means for measuring the water level in said second tank constituting said means for measuring the amount of water used to generate vapor.

4. The apparatus according to claim 3, wherein said water heating means comprise temperature regulators.

5. The apparatus according to claim 3, wherein said first tank is arranged below said mannequin body, the said cavity of which forms a top of said first tank.

6. The apparatus according to claim 3, wherein said mannequin body is made of a net of rigid material, with which a footing constituted by said first tank is associated.

7. The apparatus according to claim 2, further comprising temperature sensing means and humidity sensing means, which are arranged inside said cavity.

8. The apparatus according to claim 7, further comprising means for measuring the power used for the operation of said water vapor generation means.

9. The apparatus according to claim 8, wherein said power measurement means comprise a wattmeter for measuring the power dissipated by at least one resistive heating element which constitutes said means for heating the water that is present in said first tank.

10. The apparatus according to claim 9, comprising at least one central electronic management and control unit adapted to receive electrical signals from components of said apparatus.

11. The apparatus according to claim 10, wherein the temperature sensing means are interfaced with said at least one central electronic management and control unit.

12. The apparatus according to claim 10, wherein said humidity sensing means are interfaced with said at least one central electronic management and control unit.

13. The apparatus according to claim 10, wherein said at least one resistive element is interfaced with said at least one central electronic management and control unit.

14. The apparatus according to claim 10, wherein said wattmeter is interfaced with said at least one central electronic management and control unit.

15. The apparatus according to claim 7, wherein said temperature sensing means are constituted by thermocouple sensors, while said humidity sensing means are constituted by capacitive sensors.

16. The apparatus according to claim 7, further comprising additional temperature sensing means and humidity sensing means, which are arranged in contact with, or at a certain distance from, an outer surface of said external surface covering.

17. The apparatus according to claim 1, wherein said external surface covering for said mannequin body is made of textile material.

18. The apparatus according to claim 1, further comprising means for dressing and undressing the mannequin body and associated with said external surface covering for facilitating fitting and removing said external surface covering on and from said mannequin body.

* * * * *